(12) United States Patent
Stone et al.

(10) Patent No.: US 8,374,683 B2
(45) Date of Patent: Feb. 12, 2013

(54) MEDICAL INSTRUMENT WITH PROBE, PROBE COVER, AND METHODS OF USING THE SAME

(76) Inventors: Ray D. Stone, Camillus, NY (US); David E. Quinn, Auburn, NY (US); John A. Lane, Weedsport, NY (US)

( * ) Notice: Subject to any disclaimer, the term of this patent is extended or adjusted under 35 U.S.C. 154(b) by 386 days.

(21) Appl. No.: 12/649,595

(22) Filed: Dec. 30, 2009

(65) Prior Publication Data
US 2011/0160595 A1   Jun. 30, 2011

(51) Int. Cl.
*A61B 6/00* (2006.01)
(52) U.S. Cl. ......... 600/476; 600/179; 600/184; 600/200
(58) Field of Classification Search .................. 600/112, 600/179, 184, 200, 300, 474–476, 549, 559; 604/187; 705/2; 709/217
See application file for complete search history.

(56) References Cited

U.S. PATENT DOCUMENTS

| 5,159,936 | A | * | 11/1992 | Yelderman et al. ........... 600/549 |
| 5,991,652 | A | | 11/1999 | Barthelemy et al. |
| 6,358,216 | B1 | | 3/2002 | Kraus et al. |
| 2001/0021218 | A1 | | 9/2001 | Fukura et al. |

FOREIGN PATENT DOCUMENTS
EP   2123214 A1   11/2009

OTHER PUBLICATIONS

Notification of Transmittal of the International Search Report and The Written Opinion of the International Searching Authority, or the Declaration, Sep. 16, 2011, 9 pgs.

* cited by examiner

*Primary Examiner* — Brian Casler
*Assistant Examiner* — Daniel Huntley

(57) ABSTRACT

A medical instrument including a probe adapted to be inserted into an orifice of an animal's body. The instrument includes an emitter of electromagnetic radiation that is sensed by a sensor mounted on the probe. The sensor can then determine, by variations in the amount of radiation received from the emitter, whether a probe cover is mounted over the probe. A sensor can also be used to determine whether the walls of the body orifice block the radiation received from the emitter, thereby indicating position of the sensor, and thus, the probe within the orifice. A special probe cover is disclosed, and methods of using the medical instrument are also disclosed.

24 Claims, 3 Drawing Sheets

MEDICAL INSTRUMENT WITH PROBE, PROBE COVER, AND METHODS OF USING THE SAME

FIELD OF THE INVENTION

The present invention relates a medical instrument with a probe adapted to be inserted into an orifice in an animal's body, such as an animal's ear. In one aspect of the invention the medical instrument includes a system for determining the status of a probe cover adapted to be mounted over the probe, and in another aspect, the invention relates to a system for determining the depth of insertion of the probe into the orifice.

BACKGROUND OF THE INVENTION

Medical instruments are often inserted into body orifices in order to examine the condition of internal body tissue and other body conditions, to apply medicines, and for other purposes. Typically, such medical instruments include a probe having a generally conical peripheral configuration that is inserted into the orifice and that usually is seated against the walls of the orifice. Such medical instruments include ear instruments such as, for example, otoscopes for examining a patient's ear, infrared thermometers for measuring the temperature of an ear drum, and tympanometers.

Medical instruments that are adapted to be inserted into a body orifice are usually expensive and must be reused. The probe section of the medical instrument that is adapted to be inserted into the orifice may be contaminated with body fluids, wax, hair, and skin cells. By reusing the medical instrument, such contaminates may be transmitted to other patients, which naturally may result in the transmission of disease or other undesirable effects. In order to provide for sanitary reuse of such medical instruments, disposable probe covers have been utilized. Such probe covers are typically hollow and usually possess a configuration conforming to that or the associated probe. Probe covers may be selectively mounted to the medical instrument, in a position mounted over and around the probe, such as by a compressive snap fit or by a threadable connection. After using the medical instrument with the probe cover in connection with one patient, die probe cover is detached from the medical instrument and permanently discarded. A new probe cover is then mounted over the probe and selectively attached to the medical instrument before the medical instrument is reused with another patient.

Sometimes a healthcare practitioner may incorrectly presume that a probe cover mounted on the medical instrument is a fresh probe cover rather than one that has already been used. In such event, the probe cover may transmit contaminants to the next patient on which the medical instrument is used Aspects of the present invention were developed in response to concerns about cross-contamination due to errant reuse of a probe cover.

Another aspect of the present invention is directed to determining a depth of insertion of the probe and probe cover, and preferably whether the probe and probe cover have achieved a minimal or preferred depth of insertion when inserted into a body orifice, such as an car. In this regard, aspects of the current invention augment the teachings disclosed in Applicant's co-pending U.S. Ser. No. 12/610,760 entitled "THERMOMETER FOR DETERMINING THE TEMPERATURE OF AN ANIMAL'S EAR DRUM AND METHOD OF USING SAME", filed Nov. 2, 2009, the disclosure of which is hereby incorporated by reference.

In order to perform some procedures, the medical instrument will not properly function unless the probe is inserted to a sufficient depth, or an ideal depth, into a body orifice. Therefore it is important to determine the depth of insertion of the probe and any probe cover as a medical instrument is being used, in order to insure that the medical instrument is accomplishing its intended purpose. For example, as explained in more detail in the previously mentioned co-pending patent application, when measuring the temperature of an animal's car drum based upon the infrared radiation emitted by the ear drum, it is important that the probe be inserted sufficiently into the ear so that essentially only infrared radiation emitted by the region around the ear drum is registered. If the probe is not sufficiently inserted into the ear, then the infrared thermometer will receive infrared radiation from other areas of the ear canal and the outer ear that do not accurately indicate the temperature of the car drum. The medical instrument of the present invention may also be used to determine the depth of insertion of the probe and any probe cover.

SUMMARY OF THE INVENTION

The present invention relates to the medical instrument including a probe adapted to be inserted into an orifice of an animal's body. The instrument includes an emitter of electromagnetic radiation that is sensed by a sensor mounted on the probe. The sensor can then determine., by variations in the amount of radiation received from the emitter, whether a probe cover is mounted over the probe. A sensor can also be used to determine the extent to which the walls of the body orifice block the radiation received from the emitter, thereby indicating the position of the sensor, and thus, the position of the probe within the orifice. A special probe cover is disclosed, and methods of using the medical instrument are also disclosed.

In one embodiment, the probe cover is fashioned of a material, treated with a coating, or otherwise designed to partially transmit radiation within a selected bandwidth. The bandwidth of partial transmittance may be selected to be within, coincide with, or overlap a bandwidth of relatively intense radiation emitted by the emitter.

In other embodiments, the invention includes a microprocessor with a timer that is programmed either to generate a signal or to disable the instrument if a minimum time interval has passed since the probe cover was mounted over the probe and the sensor has not sensed the removal of the probe cover. If the system detects that the probe cover has been inserted into a body orifice by blockage of the radiation sensed by the sensor, then the microprocessor may be programmed either to generate a signal or to disable the instrument if a minimum time interval has passed since the insertion and the sensor has not sensed the removal of the probe cover.

BRIEF DESCRIPTION OF THE DRAWINGS

The invention will he described with reference to the accompanying, drawings, wherein.

DESCRIPTION OF A PREFERRED EMBODIMENT

Figure 1:
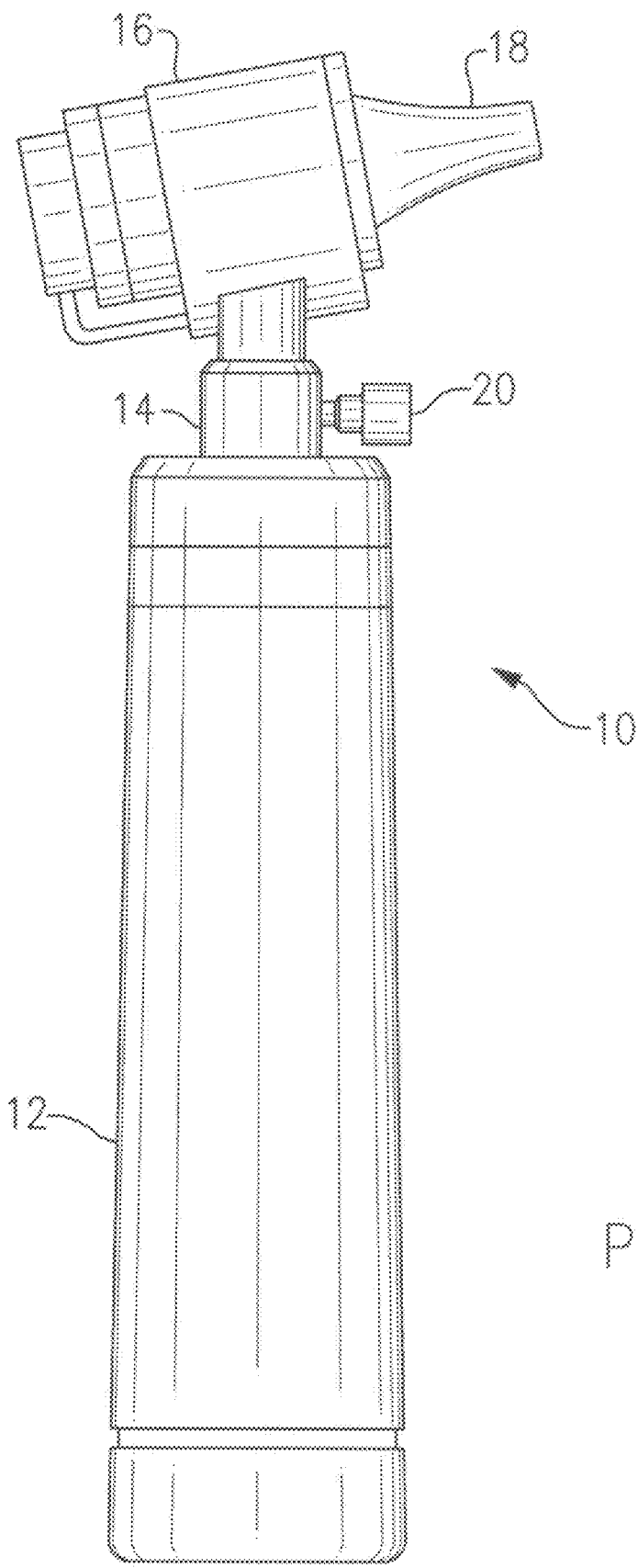
FIG. 1 is a schematic side view of an otoscope in connection with which the present invention may be used.

The present invention will be described with reference to the accompanying drawings wherein like reference numerals refer to the same item. It should be appreciated that the following description is intended to be exemplary only. and the scope of the invention envisions other variations and modifications of these particular exemplary embodiments.

There shown in FIG. 1, in general illustration, a conventional otoscope 10 that may be useful in connection with the present invention. An otoscope is a device used to examine and inspect the inner ear of a human or other animal. Although in an exemplary embodiment, reference is made to an otoscope, it should be appreciated other medical instruments, such as an infrared thermometer having a probe adapted to being inserted into a human ear, also may be advantageously employed in connection with the present invention.

The otoscope 10 includes a handle 12, a neck 14, a head section 16, and a probe 18. The neck 14 connects the head section 16 with the handle 12. Preferably, the neck 14 is constructed so that the head section 16 may be selectively rotated with respect to the handle 12 and may be selectively locked into a desired position of rotation by means of a clamping screw 20. The probe 18 generally possesses a hollow interior and both an interior and external frusto-conical configuration. The probe 18 may be attached permanently or removably from a support structure such as, for example, the head section 16.

The otoscope 10 typically has a viewing lens system and a light illumination source disposed in the head section 16. The light source projects light through the interior of the probe 18, and illuminates the ear and ear canal. The handle section 12 may house batteries that are used to power the light source. A healthcare practitioner looks through the lens system, through the interior of the probe 18, and to the illuminated area of the ear and ear canal.

It will be appreciated that direct contact of the probe 18 with the wall of the ear and ear canal will result in ear wax or other residue accumulating on the periphery of the probe 18. Reusing the same probe 18 may transmit such ear wax and other residue to another patient, which may result in the transmission of disease or other adverse effect. The probe 18 may be cleaned and sanitized, however, errors may occur by forgetting the cleaning step, or by achieving only incomplete sanitation. Moreover, patients may he reluctant to believe that the probe 18 has been sufficiently sanitized, and therefore may be reluctant to allow the healthcare practitioner to insert the probe 18 into their ears.

Figure 2A:
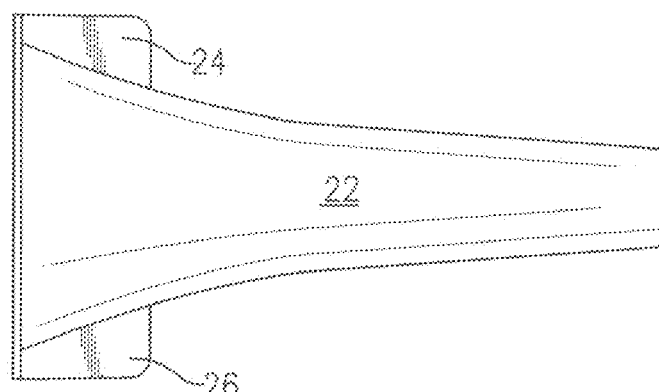
FIG. 2A and 2B are a schematic side view, and a schematic perspective view, respectively, of a probe cover that may be used in connection with the present invention.
Figure 2B:
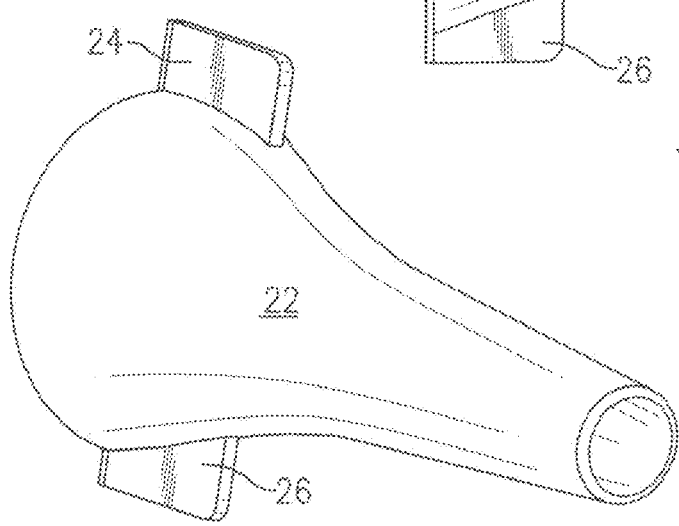

In recognition of these sanitation concerns, disposable probe covers are mounted over the probe 18 and are removably attached to the head section 16. An exemplary probe cover 22 is shown in FIGS. 2A and 2B. The probe cover 22 is fashioned as a hollow tube. Typically, a probe cover 22 possesses a generally uniform thickness, so that the exterior surface possesses a configuration that is generally similar to the interior surface of the probe cover 22. The probe cover 22 may be removably attached to the head section 16 of the otoscope 10 such as through a snap-fit connection or through a threadable connection. The probe cover 22 shown in FIGS. 2A and 2B possesses a series of internal threads so that the probe cover 22 is threadably, realeasably secured to the head section 16. For this purpose, the probe cover 22 possesses a pair of opposing fins 24, 26 by which a healthcare practitioner may manually grasp and rotate the probe cover 22. The probe cover 22 is designed for one-time use, and is intended to be disposed in the trash after use on a patient.

Figure 4:
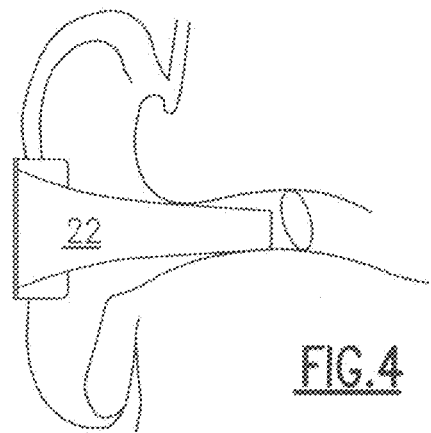
FIG. 4 is a schematic illustration of the probe and attached probe cover shown in FIG. 3 inserted into a human's ear canal.

FIG. 4 illustrates how the probe cover 22 is typically inserted into a human's ear, and helps to highlight how ear wax and other residue may come into contact with the probe cover 22 and may be carried by the probe cover 22 after removal of the probe cover 22 from the ear.

Since probe covers are disposable, they provide more confidence that contamination will not be transmitted, however, there may be errors in making sure that a probe cover is detached and discarded after use on a patient.

Figure 3:
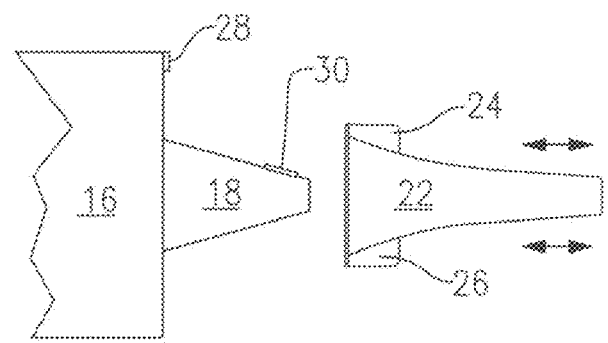
FIG. 3 is a schematic illustration of a probe in the otoscope shown on FIG. 1 in which art emitter of radiation is mounted on the head section of the otoscope, sensor is mounted on the probe of the otoscope, and a probe cover as shown in FIGS. 2A and 2B may be attached and detached from the otoscope in the directions shown by the indicated arrows.

One aspect of the present invention provides a safeguard for helping to insure that the medical instrument, such as the otoscope 10, will not be reused on a different patient with the same probe cover. As shown in FIG. 3, an emitter 28 is preferably mounted on the head section 16 of the otoscope 10. The emitter 28 is capable of emitting electro-magnetic radiation, which is directed at least in part to a sensor 30 mounted on the outside periphery of the probe 18. Preferably the electro-magnetic radiation is different from sunlight or other ambient light that: might exist in a medical facility. The radiation need not be in the visible spectrum, but preferably is within the visible spectrum. In a preferred embodiment, the emitter, comprises a blue LED that emits visible light intensely in a bandwidth of approximately 500-550 nanometers of wavelength. The radiation may be emitted continuously, or in pulses.

When the probe cover 22 is mounted over and covers the probe 18, and is detachably connected to the head section 16, radiation emitted by the emitter 28 passes; if at all, through the wall of probe cover 22 before reaching and being detected by the sensor 30. If the probe cover wall 22 is not completely transparent and not completely opaque to the radiation, the sensor 30 will he able to detect a reduction in the amount of radiation being received from the emitter 28. In order to help determine that the reduction in radiation received by the sensor 30 is due to mounting of the probe cover 22 over the probe 18, and is not due to human fingers, paper, or another abject being interposed in the path between the emitter 28 and the sensor 30, rho probe cover 22 may be selectively constructed with special characteristics that will help ensure that the reduction in sensed radiation is due to the mounting of the probe cover 22 over the probe 18. For example, it may be desirable for the probe cover 22 to have known transmittance in the range of about 40 to 60%, or about 50%, within a pre-determined bandwidth. In order to achieve such desirable transmittance, the probe cover 22 may be fashioned of a particular type of translucent material and a particular thickness designed to achieve such desired transmittance. The material forming the probe cover 22 may also be impregnated with color or other material in order to achieve such transmittance. Further, either the exterior surface, the interior surface, or both, of the probe cover 22 may be coated with material that affects the reflection, absorption, and ultimate transmittance of radiation impinging thereon within a selected bandwidth.

The invention contemplates that: color filters such as those offered by Rosco Laboratories, Inc, located in Stamford, Conn. may be employed with the probe cover 22. Such color filters include body-colored color filters in which a colorant is integrated within a plastic substrate by mixing a dye into a melted resin, deep-dyed color filters in which a clear polyester sheet is passed through a heated solvent suffused with a dye, and surface coated color filters in which a colored material is coated onto a polyester film base.

The characteristics of the probe cover 22, especially any coatings applied to probe cover 22, may possess a unique filtering of the radiation so that only very limited bandwidth of the radiation emitted by the emitter 28 is actually received by the sensor 30. In such an embodiment, the sensor 30 could also be provided with a corresponding filter so that the overall system will properly function only if probe covers 22 having a similar filtering characteristic are employed. This process can be used to help insure that only specific types of probe covers 22 are utilized in connection with the otoscope 10.

It will also be appreciated that when the probe cover 22 has moved away from the probe 18, the sensor 30 will detect an increase in the amount of radiation emitted by emitter 28. The amount of such radiation detected will correspond with the amount of radiation originally detected by the sensor 30, prior to mounting the probe cover 22 onto the head section 16 and over the probe 18.

Although the emitter 28 is shown as being mounted on the head section 16, it should be appreciated that the emitter 28 may be situated at a variety of locations, and need not be mounted on the head section 16.

Figure 5:
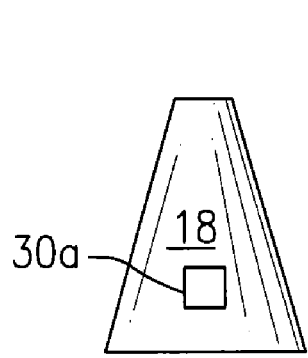
FIG. 5 is a schematic illustration of a side view of a probe on which a sensor according to one embodiment of the present invention is mounted.
Figure 6:
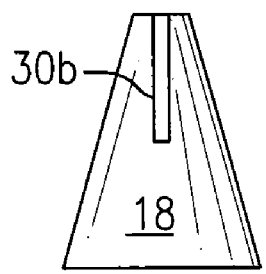
FIG. 6 is a schematic illustration of a side view of a probe on which another sensor in accordance with another embodiment of the present invention is mounted.
Figure 7:
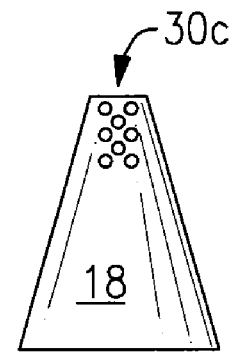
FIG. 7 is a schematic illustration of a side view of a probe on which another sensor in accordance with yet another embodiment of the present invention is mounted.

FIGS. 5, 6, and 7 illustrate different sensor configurations and positions that may be utilized in connection with a preferred embodiment of the invention. As shown in FIG. 5, the sensor 30a possesses a square configuration and is situated near ID the large end of the probe 18. In FIG. 6 the sensor 30b is fashioned in the shape of an elongate stop generally extending in a longitudinal direction relative to the probe 18 and extending from the small end thereof to approximately the mid-point longitudinally along the probe 18. In FIG. 7 the sensor 30c comprises an array of circular sensor elements mounted near the smaller end of the probe 18. Preferably the sensors 30a, 30b, 30c are oriented such that they directly face the emitter 28.

Figure 8:
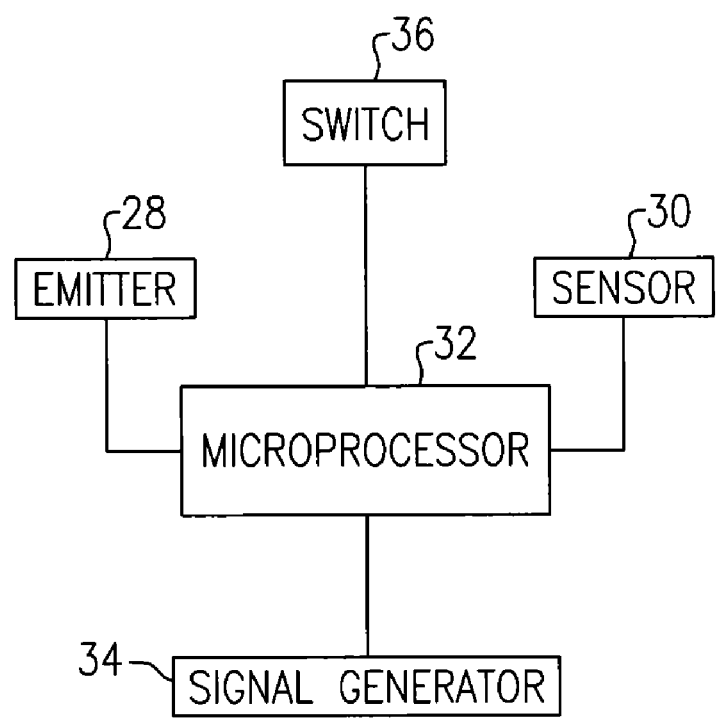
FIG. 8 is a block diagram of electrical interconnections between various components of the medical instrument in accordance with an embodiment of the present invention.

In use, the sensor 30 first determines whether the probe cover 22 has been mounted on the head section 16. As shown in FIG. 8, the sensor 30 may be operatively connected to a microprocessor 32, which may contain a timer, and which may cause a signal generator 34 to display the amount of time that has lapsed since the probe cover 22 has been mounted on the head section 16. A healthcare practitioner operating the otoscope 10 may realize from the amount of time displayed that the probe cover 22 probably has been used and should be discarded, or, as just a precautionary measure, the probe cover 22 should be discarded.

The invention also contemplates that the microprocessor 32 will be programmed to wait a predetermined time interval, such as five seconds, after the sensor 30 first senses that the amount: of radiation sensed indicates that the probe cover 22 has been mounted over the probe 1$ to register the event when the probe cover 22 has been mounted. Such a time interval will help insure that the probe cover 22 is not simply in the process of being mounted, but in fact has been mounted, Over the probe IS and is attached to the head section 16. In another embodiment, the microprocessor 32 may be programmed to register that the probe cover 22 is mounted on the head section 16 only after a predetermined time interval, such as live seconds, continuously shows that the amount of radiation sensed by sensor 30 corresponds with the probe cover 22 having been mounted over the probe 18. As an additional feature of the invention, the microprocessor 32 may be programmed so as to sound an audio alarm, or to provide a blinking light signal, via the signal generator 34 if a predetermined time interval, such as five minutes, has occurred after the sensor 30 first indicates that the probe cover 22 has been mounted the head section 16. The microprocessor 32 would be programmed not to cause such signals to be generated if the sensor 30 senses an amount of radiation that indicates that the probe cover 22 has been removed from the head section 16 and away from the probe 18 during that time interval.

The present invention contemplates that the emitter 28, such as a blue LED, might automatically provide visual illumination in a continuous manner upon removal of the otoscope 10 from a storage housing. Alternatively, as shown in FIG. 8, a switch 36 may be used to selectively activate and deactivate the emitter 28. In such it mode of operation, the emitter 28 may help a healthcare practitioner find probe covers, the patient's orifice, and other objects in a dark environment. In other embodiments of the present invention, the microprocessor 32 could disable the light source within the head section 16 from projecting light through the probe 18 unless the sensor 30 detects an amount of radiation that indicates that: a probe cover 22 is not mounted on the head section 16 or has not been removed after a predetermined time interval. In yet another embodiment, where the medical instrument is an infrared thermometer, the microprocessor 32 could prevent the thermometer from taking any temperature readings unless the sensor 30 senses an amount of radiation that indicates a probe cover 22 is mounted on the head section 16. Similarly, the microprocessor 32 could prevent the infrared thermometer from making a temperature reading if, within a predetermined time interval after the probe cover 22 has been mounted over the probe 18, the sensor 30 does not sense an amount of radiation emitted by the emitter 28 that indicates the probe cover 22 has been unmounted from the head section 16 and removed away from the probe 18.

It should also be appreciated that the present invention may be useful in connection with determining the depth of insertion of the probe 18 and any associated probe cover 22 into an orifice of a body. With special reference to FIGS. 4, 6, and 7, if the sensor 30b, 30c is disposed in the orifice near the walls of the orifice, then radiation emitted by emitter 28 will be substantially blocked or occluded from reaching the sensor 30b, 30c. Such blockage or occlusion will decrease the amount of radiation sensed by the sensor 30, which may be correlated with a particular depth of insertion of the small end of the probe 18 or the probe cover 22 within the orifice. In one embodiment, there is a linear correlation between the degree of reduction of sensed radiation with the depth of insertion. In the case of an infrared thermometer, the microprocessor 32 may be programmed to prevent a temperature reading if the depth of insertion is insufficient. Also, the recognition by the microprocessor 32 that the probe 18 and any associated probe cover 22 has been inserted into the orifice may be used to prompt the microprocessor 32 to cause the signal generator, 34 to generate an audio or visual signal or to prevent re-use of the medical instrument, such as by disabling the light source in the head section 16 in an otoscope or by disabling; the temperature reading function of an infrared thermometer, if a pre-determined time interval has passed and the sensor 30 does not indicate that the probe cover 22 has been removed. In this regard, the switch 36 may be a multi-position switch with including one position to activate or deactivate the emitter 28, and another position to activate the insertion depth function.

While exemplary embodiments have been presented in the foregoing description of the invention, it should be appreciated that a vast number of variations within the scope of the invention may exist. The foregoing examples are not intended to limit the nature or the scope of the invention in any way. Rather, the foregoing detailed description provides those skilled in the art with a foundation for implementing other exemplary embodiments of the invention.

We claim:

1. A medical instrument including
   a support structure;
   a probe attached on said support structure, said probe possessing an outer peripheral surface and adapted to be inserted into an orifice in an animal's body;
   an emitter that emits electro-magnetic radiation toward said outer peripheral surface of said probe, said emitter mounted on said support structure;
   a sensor adapted to sense said radiation, said sensor mounted on said outer peripheral surface of said probe in a position so as to receive said radiation;
   a probe cover adapted to be selectively mounted over and to substantially cover said probe and said sensor, said probe cover being partially transparent to said radiation such that when said probe cover substantially covers said probe, said sensor senses reduced transmittance of said radiation; and
   a microprocessor operatively connected to said sensor, said microprocessor configured to monitor the magnitude of said radiation sensed by said sensor and to evaluate the degree of any reduction of said monitored magnitude as an indication of the insertion of said probe into the body orifice.

2. A medical instrument according to claim 1 wherein said emitter comprises a blue LED and wherein said radiation possesses a strong intensity in the bandwidth substantially in the range of about 500-550 nanometers.

3. A medical instrument according to claim 1 wherein said probe cover transmits between about 40-60 percent of said radiation impinging thereon within a selected bandwidth.

4. A medical instrument according to claim 1 wherein said probe cover is coated with a material that blocks a substantial portion of said radiation within a selected bandwidth from passing therethrough.

5. A medical instrument according to claim 1 wherein said probe cover possesses a substantially frusto-conical configuration.

6. A medical instrument according to claim 1 wherein said medical instrument consists essentially of an ear instrument.

7. A medical instrument according to claim 1 wherein said medical instrument consists essentially of an infrared thermometer.

8. A medical instrument according to claim 1 wherein said probe extends in a substantially longitudinal direction and possesses an outer exterior surface, wherein said sensor extends in a substantially elongate, longitudinal direction along said outer peripheral surface of said probe and whereby when said probe is inserted into the orifice, said radiation is partially blocked by the walls of the orifice from reaching said sensor and as said probe is inserted deeper into the orifice even more of said radiation is blocked by the walls of the orifice from reaching said sensor.

9. A medical instrument according to claim 8 wherein said microprocessor is configured to calculate a depth of insertion of said probe into the orifice in a substantially linear relationship with the decrease in the magnitude of said radiation sensed by said sensor.

10. A medical instrument according to claim 9 wherein said microprocessor is further programmed to determine that a pre-determined depth of insertion constitutes a preferred position of said probe, wherein said medical instrument further comprises a signal generator operatively connected to said microprocessor adapted to signal whether the pre-determined depth is attained.

11. A medical instrument according to claim 10 wherein said signal generator is selected from the group consisting of a visual display screen, a sound alarm, and a visual light.

12. A method of determining the condition of a probe cover adapted to substantially cover a probe, which is adapted to be inserted into an orifice in an animal's body, comprising:
    (a) providing a medical instrument including:
        (1) a support structure;
        (2) a probe attached to said support structure, said probe possessing an outer peripheral surface and adapted to be inserted into an orifice in an animal's body;
        (3) an emitter that emits electro-magnetic radiation toward said outer peripheral surface of said probe, said emitter mounted on said support structure;
        (4) a sensor adapted to sense said radiation, said sensor mounted on said outer peripheral surface of said probe in a position so as to receive said radiation; and
        (5) a probe cover adapted to be selectively mounted over and to substantially cover said probe, said probe cover being partially transparent to said radiation;
    (b) emitting said radiation from said emitter;
    (c) sensing said radiation with said sensor;
    (d) monitoring the magnitude of said radiation sensed by said sensor;
    (e) establishing a threshold magnitude of said radiation;
    (f) setting a threshold time interval; and
    (g) determining that said probe cover is mounted over and substantially covers said probe if said monitored magnitude of said radiation is no more than said threshold magnitude during said threshold time interval.

13. A method of determining the condition of a probe cover adapted to substantially cover a probe, which is adapted to be inserted into an orifice in an animal's body, according to claim 12, further comprising:
    (h) if it is determined that said probe cover has been mounted over and substantially covers said probe, then making a later determination of whether the magnitude of said radiation sensed by said sensor increases by a magnitude that would indicate that such probe cover has been unmounted from a disposition mounted over and substantially covering said probe.

14. A method of determining the condition of a probe cover adapted to substantially cover a probe, which is adapted to be inserted into an orifice in an animal's body, according to claim 13, further comprising:
    waiting a pre-determined time interval after the earlier determination that said probe cover has been mounted over and substantially covers said probe before making said later determination.

15. A method of determining the condition of a probe cover adapted to substantially cover a probe, which is adapted to be inserted into an orifice in an animal's body, according to claim 13 further comprising:
    generating a signal if the later determination indicates that the magnitude of said radiation sensed by said sensor is not increased by a magnitude that would indicate that said probe cover has been unmounted from a disposition mounted over and substantially covering said probe within a predetermined time interval after the earlier determination indicates that said probe cover has been mounted over and substantially covers said probe, said signal selected from the group consisting of a visual display screen, a sound alarm, and a visual light.

16. A method of determining the condition of a probe cover adapted to substantially cover a probe, which is adapted to be inserted into an orifice in an animal's body, according to claim 13 wherein said medical instrument comprises an infrared thermometer in which the probe thereof is adapted to be inserted into an ear and further comprising preventing said thermometer from reading a temperature if the later determination indicates that the magnitude of said radiation sensed by said sensor is not increased by a magnitude that would indicate that said probe cover has been unmounted from a disposition mounted over and substantially covering said probe within a predetermined time interval after the earlier determination indicates that said probe cover has been mounted over and substantially covers said probe.

17. A method of determining the depth of insertion of a probe of a medical instrument into an orifice of a body, comprising:
   (a) providing a medical instrument including:
      (1) a support structure;
      (2) a probe attached to said support structure, said probe possessing an outer peripheral surface and adapted to be inserted into an orifice in an animal's body;
      (3) an emitter that emits electro-magnetic radiation toward said outer peripheral surface of said probe, said emitter mounted on said support structure;
      (4) a sensor adapted to sense said radiation, said sensor mounted on said outer peripheral surface of said probe in a position so as to receive said radiation;
   (b) emitting said radiation from said emitter;
   (c) sensing said radiation with said sensor;
   (d) determining the magnitude of said radiation sensed by said sensor;
   (e) inserting said probe into the orifice;
   (f) monitoring the magnitude of said radiation sensed by said sensor as said probe is inserted into the orifice; and
   (g) evaluating whether the degree of any reduction of said monitored magnitude as said probe is inserted into the orifice indicates the extent to which said sensor has passed a wall of the orifice.

18. A method of determining the depth of insertion of a probe of a medical instrument into an orifice of a body according to claim 17 further comprising:
   determining the depth of insertion of said probe into the orifice based upon said evaluation.

19. A method of determining the depth of insertion of a probe of a medical instrument into an orifice of a body according to claim 17 wherein said probe extends in a substantially longitudinal direction and wherein said sensor extends in a substantially elongate, longitudinal direction along said outer peripheral surface of said probe.

20. A method of determining the depth of insertion of a probe of a medical instrument into an orifice of a body according to claim 17 wherein said sensor comprises an array of sensor elements mounted on said probe.

21. A method of determining the condition of a probe cover adapted to substantially cover a probe, which is adapted to be inserted into an orifice in an animal's body, comprising:
   (a) providing a medical instrument including:
      (1) a support structure;
      (2) a probe attached to said support structure, said probe adapted to be inserted into an orifice in an animal's body;
      (3) an emitter that emits electro-magnetic radiation toward said probe, said emitter mounted on said support structure;
      (4) a sensor adapted to sense said radiation, said sensor mounted on said probe in a position so as to receive said radiation; and
      (5) a probe cover adapted to be selectively mounted over and to substantially cover said probe, said probe cover being partially transparent to said radiation;
   (b) emitting said radiation from said emitter;
   (c) sensing said radiation with said sensor;
   (d) determining the magnitude of said radiation sensed by said sensor;
   (e) assessing whether the magnitude of said radiation sensed by said sensor drops by a magnitude that would indicate that said probe cover has been mounted to substantially cover said probe; and
   (f) if the magnitude assessment indicates that said probe cover has been mounted to substantially cover said probe, then making a later magnitude assessment of whether the magnitude of said radiation sensed by said sensor increases by a magnitude that would indicate that such probe cover has been unmounted from a disposition substantially covering said probe.

22. A method of determining the condition of a probe cover adapted to substantially cover a probe, which is adapted to be inserted into an orifice in an animal's body, according to claim 21, further comprising:
   waiting a pre-determined time interval after the earlier magnitude assessment indicates that said probe cover has been mounted to substantially cover said probe before making said later magnitude assessment.

23. A method of determining the condition of a probe cover adapted to substantially cover a probe, which is adapted to be inserted into an orifice in an animal's body, according to claim 21 further comprising:
   generating a signal if the later magnitude assessment indicates that the magnitude of said radiation sensed by said sensor does not increase by a magnitude that would indicate that said probe cover has been unmounted from a disposition substantially covering said probe within a predetermined time interval after the prior radiation magnitude assessment indicates that said probe cover has been mounted to substantially cover said probe, said signal selected from the group consisting of a visual display screen, a sound alarm, and a visual light.

24. A method of determining the condition of a probe cover adapted to substantially cover a probe, which is adapted to be inserted into an orifice in an animal's body, according to claim 21 wherein said medical instrument comprises an infrared thermometer in which the probe thereof is adapted to be inserted into an ear and further comprising preventing said thermometer from reading a temperature if the later magnitude assessment indicates that the magnitude of said radiation sensed by said sensor does not increase by a magnitude that would indicate that said probe cover has been unmounted from a disposition substantially covering said probe within a predetermined time interval after the earlier magnitude assessment indicates that said probe cover has been mounted to substantially cover said probe.

* * * * *